United States Patent
Lowman et al.

(10) Patent No.: US 7,736,619 B2
(45) Date of Patent: Jun. 15, 2010

(54) HYDROGEL COMPOSITIONS AND MANUFACTURING PROCESS FOR ULTRASOUND COUPLANTS

(75) Inventors: Anthony M. Lowman, Wallingford, PA (US); Larry L. Smith, Lummi Island, WA (US)

(73) Assignee: UST Inc., Bothell, WA (US)

( * ) Notice: Subject to any disclaimer, the term of this patent is extended or adjusted under 35 U.S.C. 154(b) by 995 days.

(21) Appl. No.: 10/978,767

(22) Filed: Nov. 1, 2004

(65) Prior Publication Data

US 2005/0095296 A1    May 5, 2005

Related U.S. Application Data

(60) Provisional application No. 60/517,555, filed on Nov. 5, 2003.

(51) Int. Cl.
*A61B 8/00* (2006.01)
*A61K 49/00* (2006.01)

(52) U.S. Cl. .......................... 424/9.1; 424/9.5

(58) Field of Classification Search ............... 424/9.5
See application file for complete search history.

(56) References Cited

U.S. PATENT DOCUMENTS

| 4,663,358 | A | * | 5/1987 | Hyon et al. | 521/64 |
|---|---|---|---|---|---|
| 5,106,876 | A | * | 4/1992 | Kawamura | 522/5 |
| 5,575,291 | A | | 11/1996 | Hayakawa | |
| 6,039,694 | A | | 3/2000 | Larson et al. | |
| 2004/0234453 | A1 | * | 11/2004 | Smith | 424/9.5 |

* cited by examiner

*Primary Examiner*—Michael G Hartley
*Assistant Examiner*—Melissa Perreira
(74) *Attorney, Agent, or Firm*—Robert L. McDowell

(57) ABSTRACT

A hydrogel coupling device for the transmission of ultrasound therethrough having a predetermined shape and comprising a hydrogen bonded composition comprising PVA, one or both of PVP and PEG, and the balance water. The predetermined shapes are formed and are then exposed to (a) one or more freeze/thaw cycles, (b) one or more dehydration/re-hydration cycles, or (c) one or more freeze/thaw cycles and one or more dehydration/re-hydration cycles. The shapes may further be irradiated with high energy radiation followed by heat treating.

8 Claims, No Drawings

HYDROGEL COMPOSITIONS AND MANUFACTURING PROCESS FOR ULTRASOUND COUPLANTS

This application claims the benefit of U.S. Provisional Patent Application No. 60/517,555 filed Nov. 5, 2003.

FIELD OF THE INVENTION

The present invention is directed to compositions and processes for manufacture of hydrogels for medical ultrasound imaging and therapy.

Background of the Invention

When ultrasound energy is used in medical applications, it generally falls in the frequency range of 0.5 to 15 and as high as 20 MHz. The ultrasound frequency used is dependent upon the application. For instance, imaging of deep organs such as the liver, kidney and certain fetal scans utilize frequencies in the range of 2.0 to 5.0 MHz. When near surface resolution is required as when imaging the eye, frequencies of 10 and 20 MHz are required. In therapeutic applications like heating of muscle and tissue, ultrasound frequencies below 1.0 MHz are generally used. Recent advances include the use of high intensity focused ultrasound (HIFU) ultrasound for hemostasis and ablation, usually using frequencies of 2 to 8 MHz., of the liver and spleen as well as sealing of holes in lungs.

The use of ultrasound for medical applications requires that the ultrasound energy be conducted or coupled into and reflected from, in the case of imaging, to the site that is being examined or treated. Sound waves at these frequencies are attenuated by air. However, sound waves can be efficiently transmitted from the ultrasound source, generally referred to as an ultrasound transducer, into and reflected from a target of interest by use of substances that efficiently transmits ultrasound energy and eliminates air between the face of the transducer the surface of the site being examined or treated.

These ultrasound coupling or conductive substances are well known in medical diagnostic imaging and industrial applications involving non-destructive testing (NDT). Commonly used materials include gels made from natural polysaccharides and synthetic polymers, such as CARBOPOL. In addition to gel forms, efficient ultrasound couplers include membranes and solid materials that contain water, and known in the trade as hydrogels. When used for medical applications, the greatest ultrasound transmission efficiencies are realized when the coupling media is similar to human tissue. U.S. Pat. No. 6,039,694 to Larson et al. describes a solid ultrasound coupling membrane formed by extraction of a thiocyanate ion in exchange with water to coagulate a hydrogel from a polyacrylonitrile co-polymer that is strong, flexible and contains water sufficient to promote acceptable mechanical and acoustic properties for use in medical ultrasound applications.

U.S. Pat. No. 5,575,291 to Hayakawa describes a production technique to form a solid hydrogel produced by repeated freeze thaw cycles of polyvinyl alcohol (PVA) solutions to create a solid ultrasound coupler and standoff. The method involves injection of a 3 to 6% aqueous solution PVA, having a degree of saponification of not less than 98%, into a mold that is then subjected to one or more freeze-thaw cycles to form a solid. The device of Hayakawa is a solid and requires attachment of the coupling member to an ultrasound probe for use. Furthermore, Hayakawa relies solely upon the use of polyvinyl alcohol solutions without reference or example to other primary and active components in combination with PVA. In Hayakawa, transformation of polyvinyl alcohol solutions from a flowable liquid to a solid can be done only through the process of freeze-thaw cycles.

SUMMARY OF THE INVENTION

The present invention describes the use and formulation of polyvinyl alcohol in combination with other polymers, such as polyvinylpyrrolidone and polyethylene glycols, with water to form hydrogels for use as coupling, delay line and standoff members for ultrasound imaging and therapy. Such formulations and processing techniques provide for hydrogels that can form strong structures, with high durometers and tensile strength, to soft gels and elastic films that all possess acoustic coupling and conducting properties with low attenuation of ultrasound energy similar to that of human and animal tissue. Such formulations can be tailored to meet a broad range of specifications.

DETAILED DESCRIPTION OF THE PREFERRED EMBODIMENTS

The present invention provides for the formulation and processes for a class of hydrogels for use in ultrasound applications that involve imaging and therapy. The formulations consist of polyvinyl alcohol (PVA) in combination with polyvinylpyrrolidone (PVP), polyethylene glycols (PEG) and water. The present invention also provides for production of hydrogels as films and solid shapes of various design that can be tailored by composition and processing techniques to create a broad range of mechanical, acoustic and optical properties specific to the end use. Parameters of composition and process for production of a family of hydrogels comprising polyvinyl alcohol, polyvinylpyrrolidone, polyethylene glycols, water and additives to retard drying and tailor mechanical properties are disclosed. Unless otherwise stated, all percentages discussed are weight percent (wt. %).

The invention is directed to formulas, process methods and use of materials that yield a broad-spectrum hydrogels with unique properties. Processing technique, polymer composition and concentration are varied to produce a range of hydrogels that can contain water concentrations approaching 100% with thin gel-like properties to solid hydrogels with high durometers and tensile properties. Within the range of these parameters, transmission of ultrasound energy is efficient, making the products of this invention suitable for use as gel couplants, membranes of various thicknesses, delay lines and stand-offs of various geometries in therapy such as HIFU (High Intensity Focused Ultrasound) and diagnostic ultrasound imaging. The processing techniques disclosed also provide methods for production of optically clear hydrogels that possess thermal properties and provide utility for their use in HIFU applications.

The physical and mechanical properties are first influenced by the ratio of polyvinyl alcohol to polyvinylpyrrolidone and or polyethylene glycols. The addition of polyvinylpyrrolidone or polyethylene glycols provides greater hydrophilicity and strength than can be achieved with polyvinyl alcohol alone. PVP and PEG additions act to increase hydrogen bonding and retention of the polymers within the hydrogel structure, whereas, the PVA component contributes the highest degree of strength to the hydrogel though crystallization.

The ratio of these compounds can be varied from 1:1 to 100:1 to 1:100 as required by product specifications. As a rule, as the ratio of PVA to PVP or PEG increases, the potential for creating hydrogels of high mechanical strength increases. Conversely, as the ratio of PVA to PVP or PEG approaches equivalence, resultant hydrogels become weaker. Polymers such as polyethylene glycols of various molecular weights can be included in the formulation to comprise a third polymer to modify the hydrogel characteristics or formulated with PVP and also to the exclusion of PVP. Compounds such as glycols when included in these formulations, can also perform as humectants to retard drying time.

In addition to the ratios of PVA/PVP/PEG in water as described above, each of these compounds is available in different molecular weights, and in the case of polyvinyl alcohol, various grades are also differentiated by the degree of hydrolysis. Although particular grades and molecular weights are preferred over others, all grades and combinations of grades and molecular weights of these compounds will respond in the manner and form taught in this invention In contrast to Hayakawa, discussed above, the formulations of the present invention are not restricted to use of freeze-thaw processing to form strong films and structures. As an alternative to freeze-thaw cycles, the devices of this invention can also be created by dehydration of the polymer solution followed by re-hydration to reform the hydrogel. If dehydration is preferred as the processing method, the film or shaped device produced can be re-hydrated with water or a combination of humectants and other additives to return to the configuration of the original form. Alternatively a combination of freeze-thaw followed by dehydration and re-hydration can be employed to achieve film clarity. Although the process of using freeze-thaw cycles is familiar in the art, such a process has been limited to use of freeze-thaw cycles in hydrogen bonding of solutions consisting exclusively of polyvinyl alcohol.

Solutions of PVA, PVP, PEG of various ratios and other compounds, such as salts alkyl alcohols and humectants such as alkyl glycols in water, generally form clear solutions of various viscosities which depend on the molecular weight of the compounds and polymer concentration. Conversion of these liquids to solids and semi-solid structural materials requires the application of freeze-thaw cycles or alternatively dehydration of the polymer solution.

The freeze-thaw technique forming hydrogels from solutions requires that the solution be first frozen for a period of time sufficient to initiate hydrogen bonding and set the dimensional characteristics. The solutions can be cast into films or into molds of varying shapes and sizes prior to the first freeze cycle. The practical length of the freeze cycle generally varies between one and twenty four hours. A freeze cycle of approximately one hour can be used to produce weak gels and freeze cycles approaching twenty-four hours are desirable for stiff hydrogel forms. Freeze cycles of six hours are generally satisfactory for a broad range of hydrogel products. The hydrogels formed from freeze-thaw cycles of these formulations are generally translucent. In instances where clarity is required, such can be achieved by partial or full dehydration followed by re-hydration. Dehydration can be accomplished by drying the freeze-thaw processed item in air or in a vacuum followed by re-hydration. When fully re-hydrated the hydrogel item becomes clear and returns to its original shape.

The number of freeze-thaw cycles also influences the physical and mechanical properties of the hydrogel forms. When the initial freeze-thaw cycle is performed, especially with short duration, limited hydrogen bonding occurs producing soft gelatinous hydrogels. As the length of the freeze period increases together with the number of freeze-thaw cycles, the level hydrogen bonding increases. In this manner, the physical and mechanical properties of the hydrogels produced can be broadly varied even within a single formulation that has been selected from within the range of potential compositions taught within this invention.

The general production method for this family of hydrogels can be summarized as preparation of a desired formulation of PVA, PVP, PEG, humectants and other compatible compounds as a solution in water. The solution is cast as a film of desired thickness or into a mold of various dimensions and shape, then subjected to a series of freeze-thaw cycles, for example, six hours freeze and one hour of thawing until the desired physical and mechanical properties are obtained. The thaw time portion of the cycle can be longer as required by dimension and configuration. Alternatively, the solution can be cast into a mold of various dimensions and dehydrated to initiate hydrogen bonding, followed by re-hydration in aqueous solutions containing salts, modifying and active agents such as, for example, sodium chloride as in a saline solution, propylene glycol, $C_2$-$C_6$ alcohols or glycerin. Although the dehydration/re-hydration cycle is usually performed once, more than one of these cycles may be carried out.

From the preceding description, it can be appreciated that the present invention contemplates a large number of combinations of chemical formulations with associated molecular weight and percentage hydrolysis differences, plus various freeze-thaw cycles, to produce hydrogels having an equal number of physical and mechanical property combinations.

The following examples are representative of formulas and process parameters that demonstrate the teaching of this invention but as examples are not inclusive of all potential combinations of ingredients and freeze-thaw cycles.

The compounds used to demonstrate the teaching of the invention are available from commercial sources. Polyvinyl alcohol Grade 71-30 (viscosity 27-33 centipoise) was obtained from Dupont, Wilmington, Del. under the product name EVANOL 71-30, and CELVOL® 350 (viscosity 62-72 centipoise) and 125 (viscosity 28-32 centipoise) was obtained from Celanese Chemical GmbH. Polyvinylpyrrolidone was sourced as KOLLIDONE K15 (molecular weight 2,000-3,000 daltons), K30 (molecular weight 44,000-54,000 daltons) and K90 (molecular weight 1,000,000-1,500,000 daltons) from BASF Corporation, Mt. Olive, N.J. Polyethylene glycols in a molecular weight range of 300 to 6,00,000 were sourced from Dow Chemical, Wilmington, Del.

The following formulations are examples can be understood to provide a basis for confirming representation of a much broader base of formulations using freeze-thaw and dehydration to formulations based on solutions of PVA, that further contain other polymers such as PVP and PEG. In addition, compounds such as propylene glycol, glycerin and $C_2$-$C_6$ alcohols may be included as humectants and/or alkaline salts may be included to adjust salinity.

The following are examples of formulations that contain total polymer concentrations of 10% and 15%. The solutions were prepared by first weighing dry PVA and PVP followed by addition to De-ionized (DI) water with stirring. The ingredients were then sealed to prevent water loss and heated with agitation to 90 degrees centigrade until solution was complete, and absence of air bubbles and homogeneity was observed. The solutions were cooled to room temperature prior to casting. Cooling prior to casting is not a prerequisite to successful processing and therefore does not limit the process where casting as a hot solution may be desirable.

EXAMPLE 1

| | |
|---|---|
| PVA DuPont Elvanol 71-30 | 95% |
| PVP BASF Kollidone K 30 | 5.0% |
| The composition and ratio of these polymers represent a total of 10% of the total solution. | |
| De-ionized Water | 90% |

EXAMPLE 2

| | |
|---|---|
| PVA Celvol 350 | 95% |
| PVP BASF Kollidone K 90 | 5.0% |
| The composition and ratio of these polymers represent a total of 10% of the total solution. | |
| De-ionized Water | 90% |

EXAMPLE 3

| | |
|---|---|
| PVA Celvol 350 | 99% |
| PVP BASF Kollidone K 90 | 1.0% |
| The composition and ratio of these polymers represent a total of 15% of the total solution. | |
| De-ionized Water | 85% |

EXAMPLE 4

| | |
|---|---|
| PVA Celvol 350 | 80% |
| PVP BASF Kollidone K 90 | 20.0% |
| The composition and ratio of these polymers represent a total of 10% of the total solution. | |
| De-ionized Water | 90% |

EXAMPLE 5

| | |
|---|---|
| PVA Celvol 350 | 70% |
| PVP BASF Kollidone K 90 | 30.0% |
| The composition and ratio of these polymers represent a total of 10% of the total solution. | |
| De-ionized Water | 90% |

EXAMPLE 6

| | |
|---|---|
| PVA Celvol 350 | 60% |
| PVP BASF Kollidone K 90 | 40.0% |
| The composition and ratio of these polymers represent a total of 10% of the total solution. | |
| De-ionized Water | 90% |

EXAMPLE 7

This formulation was prepared using the same polymer ratio as in Examples 1 and 2. However, the total concentration of the polymer in the solution was decreased to 5.0% to compare the film properties against those of the 10% polymer concentration.

| | |
|---|---|
| PVA DuPont Elvanol 71-30 | 95% |
| PVP BASF Kollidone K 30 | 5.0% |
| The composition and ratio of these polymers represent a total of 5.0% of the total solution. | |
| De-ionized Water | 90% |

A 3 mm thick casting of the material of Example 7 was made followed by four 6/1-hour freeze-thaw cycles. Subsequent to the initial freeze-thaw cycle, the consistency and relative gel strength was compared by touch and stretching to that of an identical sample prepared from the 10% solution of Example 1. The hydrogel containing was gelatinous and readily tore when stretched; whereas, the hydrogel sample containing 10% polymer demonstrated a soft well constituted solid of sufficient elasticity that resisted tearing. The toughness of both the 5% and 10% samples increased as the number of freeze thaw cycles increased. At the completion of the fourth cycle the predicted relative toughness and gel strength of the 10% polymer composition was greater than that produced by the 5% sample.

EXAMPLE 8

| | |
|---|---|
| PVA Celvol 350 | 95% |
| PVP BASF Kollidone K 90 | 2.5% |
| PEG 8000 | 2.5% |
| The composition and ratio of these polymers represent a total of 10% of the total solution. | |
| De-ionized Water | 90% |

Samples of Example 8 formulation processed by four freeze-thaw cycles, demonstrated physical and mechanical properties similar to those of Example 1.

EXAMPLE 9

| | |
|---|---|
| PVA Celvol 350 | 95% |
| PVP BASF Kollidone K 90 | 5.0% |
| The composition and ratio of these polymers represent a total of 10% of the total solution. | |
| De-ionized Water | 70% |
| Polyethylene Glycol | 20% |

The formula of Example 9 was prepared to determine the feasibility of adding propylene glycol to the formulation to act as a humectant for the purpose of extending the drying time during use. The sample was subjected to four freeze-thaw cycles of six hours freeze and 1 hour thaw. A firm translucent hydrogel formed, confirming the compatibility of propylene glycol additions to the hydrogel formation process.

Samples of each formulation were cast in petrie dishes to thicknesses of 1 and 3 mm and placed in a freezer operating at a temperature of minus 20 degrees Centigrade for a periods of 1 hour followed by thawing to room temperature for a period that achieved complete thawing of the gel. Four freeze-thaw cycles were repeated using a six hour freeze followed by a one-hour thaw period. Each sample was examined for relative strength and elasticity after each of the thaw periods and subjectively determined to exhibit increased tensile strength and an attendant reduction in elasticity.

As the ratio of PVA to PVP decreased, the resultant gel strength decreased. The gel of Example 6 exhibited characteristics of a flowable gel that was unable to maintain dimensional stability. As the ratio of PVA/PVP increased, such as the ratio of Example 1, the first freeze cycle yielded a rigid dimensionally stable hydrogel that upon subsequent freeze-thaw cycles continued to increase in rigidity and decrease in elasticity.

The concentration of the polymer solution was selected based on the relative solubility limits of PVA with the highest levels of hydrolysis and a target solution temperature of 90 degrees centigrade as a control on the temperature effects on crystallization of PVA. Concentrations of polymer above 20% using Elvanol 71-30 are limited by the solubility of this grade. PVA grades such as Celvol 103 (viscosity 3.5-4.5 centipoise) could be formulated to polymer concentrations approaching 60%, however, the water content would be in the range of 40%, which is less than desirable to match the acoustic properties of human tissue that result from water contents of 70 to 90%. As the total polymer concentration drops below 10%, the water content increases with attendant decreases in gel strength to a point where crystallization of the PVA and hydrogen bonding are of no consequence to hydrogel formation. Total polymer concentrations of 0.1% using high viscosity producing PVA (62-72 cps) to 70% using Celvol 103 and 502 (viscosity 3.0-3.7 centipoise) are within the framework of the present invention for forming hydrogen bonded solid hydrogels. Preferably, the water content should be at least about 70% to match the properties of human tissue, thereby limiting the preferred total polymer content to a maximum of about 30%.

To demonstrate hydrogen bonding and crystallization of PVA and PVP solutions using the process of dehydration without freeze/thaw processing, a second sample using the formula of Example 1 was prepared from a solution of PVA and PVP in de-ionized water. The formulation of Example 1 was cast on a glass surface to form a puddle of the solution and allowed to dry at room temperature. The temperature could be higher or lower. After total dehydration was accomplished, de-ionized water was placed on the surface of the dehydrated hydrogel to re-hydrate the film. Upon re-hydration, a hydrogen bonded, optically clear and strong film resulted.

A second sample was prepared from 30 grams of solution of Example 1 and processed using four freeze-thaw cycles of 6 hours freeze/1 hour thaw. The resultant gel was exhibited high tensile strength, minimal elasticity and was translucent. This sample was dehydrated in an oven at 38 degrees Centigrade and cooled to room temperature, then placed in de-ionized water for two days for re-hydration. The re-hydrated sample was weighed and determined to be within 10% of the original solution weight. The process of dehydration followed by re-hydration produced an optically clear film.

Samples using a solution of Example 1 were cast into cone shaped molds of approximately 40 mm in length and 35 mm at the base. The molds were placed in a −10 degree Centigrade freezer and processed through four cycles of 6 hours freeze/1 hour thaw. The resultant casting maintained the mold shape and demonstrated mechanical toughness and flexibility. The casting was however not optically clear as is desirable in some ultrasound applications.

Subsequent acoustic testing indicated that PVA/PVP hydrogels in solid form such as a cone, might be used as a coupling member for High Intensity Focused Ultrasound (HIFU) applications. HIFU can be applied for use as a means of hemostasis and tissue ablation by thermal means, whereby the tissue is heated to a temperature that denatures the cell proteins and by mechanical means through disruption of cellular and nuclear membranes caused by localized cavitation.

Since the energy requirements for HIFU to cause the therapeutic effects of hemostasis and ablation are on the order of 1,000 to 10,000 Watts/cm$^2$ using ultrasound energy at a frequency in the range of 2-9 MHz, the acoustic coupler must operate without degradation at temperatures in excess of 70 degrees Centigrade during the treatment cycle. PVA/PVP cone couplers produced by freeze/thaw techniques were tested subjected to such HIFU conditions and determined to be unsuitable for use in such applications due to lack of optical clarity and thermal degradation below the required operating temperatures which approach 100° C. PVP/PVA cone couplers produced by dehydration/re-hydration are also unsuitable for HIFU conditions due to thermal degradation. Since the structural properties of the cones primarily rely on hydrogen bonding, application of heat in the range of 70 to 80° C., the range in which PVA melts, resulted in breakdown of the weak hydrogen bonds and subsequent melting.

Production of optical clarity in freeze/thaw processed solutions has been addressed in U.S. Pat. No. 4,663,358 to Hyon et al. who teach the addition of water miscible organic solvents such as DMSO, alkyl glycols and alcohols. Hyon et al. teach that such water miscible organic solvents act to prevent formation of an ice phase which thereby decreases the production of large pores in the crystal matrix. Since the pore sizes are small, the change in refractive index is minimized and the hydrogel thus produced remains transparent. However, although the device of Hyon et al. can be made transparent, the PVA hydrogel structure is retained by the weak forces of hydrogen bonding and is unsuitable for use as acoustic couplants in HIFU applications due to its melting point less than temperatures normal to this application.

The inventors have discovered that in order to produce PVA/PVP hydrogel acoustic coupling members that meet the optical and thermal requirements discussed above, the freeze/thaw method and/or the dehydration/re-hydration method, to set the dimensions and desired mechanical properties, is preferably followed by high energy radiation and heat treatment to produce optical clarity.

Using the formula of Example 1 above, 10% solutions of PVA/PVP were cast into six cone shaped molds followed by six (6) 1 hour freeze/thaw cycles at −10 degrees C. The number of freeze/thaw cycles varied with each mold beginning with one cycle for sample one with the addition of one cycle in each subsequent sample so that Sample 1 received one cycle and Sample 6 was processed through six cycles. As the number of freeze/thaw cycles increased, the rigidity and hardness of the hydrogel cones increased. All cones so treated were subjected to gamma radiation in a dosage range of 28 to 32 kG. High energy radiation treatment is not limited to Gamma rays but include also E-beam and ultraviolet when of sufficient energy to create cross-linking.

Post-gamma treatment was followed by heat treatment that involved heating the gamma treated samples to 80° C. for 30 minutes. To limit loss of solvents during heating, the samples were vacuum sealed in 10 mil plastic pouches. Such enclosure is not limited to plastic pouches but may include any containment that prevents the loss of solvent vapors through the walls of the container. Heat treatment is successful in a temperature range of 60-90 degrees C. or higher for periods of 15 minutes to 1 hour as determined by the dimensions of the object and the time required for the temperature to reach equilibrium throughout.

Subsequent examination revealed that the PVA/PVP hydrogel cones retained original dimensions, were optically clear and due to gamma induced cross-linking exhibited increased toughness and thermal stability. Melting point studies of the pre and post heat treated samples demonstrated that the gamma irradiated PVA/PVP hydrogel retained structural integrity and did not degrade at HIFU operating temperatures of about 100° C. and did not melt at 150° C. High energy radiation induced cross-linking extends the melting temperature far beyond that of the simply hydrogen bonded hydrogel produced by freeze/thaw or dehydration/re-hydration. Degradation of the hydrogel occurred over time by evaporation of the water in the formulation.

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. A method of producing a hydrogel coupling device for the transmission of ultrasound therethrough, said method comprising:
   forming predetermined hydrogel shapes comprising PVA, one or both of PVP and PEG, and the balance water,
   exposing said hydrogel shapes to (a) one or more freeze/thaw cycles, (b) one or more dehydration/re-hydration cycles, or (c) one or more freeze/thaw cycles and one or more dehydration/re-hydration cycles
   irradiating said hydrogel shapes with high energy radiation, and,
   heat treating said hydrogel shapes until said shapes are optically clear.

2. The method of claim 1 wherein said heat treating is performed at about 60° C. or more for about 15-60 minutes.

3. The method of claim 2 wherein said heat treating is carried out at 60-90° C. for about 15 to 60 minutes.

4. The method of claim 3 wherein said heat treating is carried out at 80° C. for 30 minutes.

5. The method of claim 1 wherein said hydrogel further includes alkyl glycols and alcohols.

6. The method of claim 1 wherein said high energy radiation includes gamma, e-beam or UV.

7. The method of claim 1 wherein a freeze/thaw cycle comprises freezing for one hour or more followed by thawing.

8. The method of claim 1 wherein said ultrasound comprises High Intensity Focused Ultrasound.

\* \* \* \* \*